(12) United States Patent
Xu

(10) Patent No.: US 9,278,919 B1
(45) Date of Patent: Mar. 8, 2016

(54) SYNTHESIS OF N-(3-(5-FLUORO-2-(4-(2-METHOXYETHOXY)PHENYLAMINO)PYRIMIDIN-4-YLAMINO)PHENYL)ACRYLAMIDE

(71) Applicant: Yong Xu, San Diego, CA (US)

(72) Inventor: Yong Xu, San Diego, CA (US)

( * ) Notice: Subject to any disclaimer, the term of this patent is extended or adjusted under 35 U.S.C. 154(b) by 0 days.

(21) Appl. No.: 14/656,783

(22) Filed: Mar. 13, 2015

(51) Int. Cl.
| | |
|---|---|
| C07C 277/08 | (2006.01) |
| C07D 239/545 | (2006.01) |
| C07D 239/52 | (2006.01) |
| C07D 239/48 | (2006.01) |

(52) U.S. Cl.
CPC ............ *C07C 277/08* (2013.01); *C07D 239/48* (2013.01); *C07D 239/52* (2013.01); *C07D 239/545* (2013.01)

(58) Field of Classification Search
CPC ............... C07D 239/48; C07D 239/52; C07D 239/545; C07C 277/08
See application file for complete search history.

*Primary Examiner* — Valerie Rodriguez-Garcia
(74) *Attorney, Agent, or Firm* — Houtteman Law LLC

(57) ABSTRACT

A method for preparing BTK inhibitor CC-292 of formula 1, comprising: (1) contacting a compound of formula 2 with a compound of formula 3 to obtain a compound of formula 4; (2) contacting the compound of formula 4 with a compound of formula 5 to obtain a compound of formula 6; (3) contacting the compound of formula 6 with trifluoromethanesulfonic anhydride to obtain a compound of formula 7; and (4) contacting the compound of formula 7 with a compound of formula 8 to obtain the compound of formula 1.

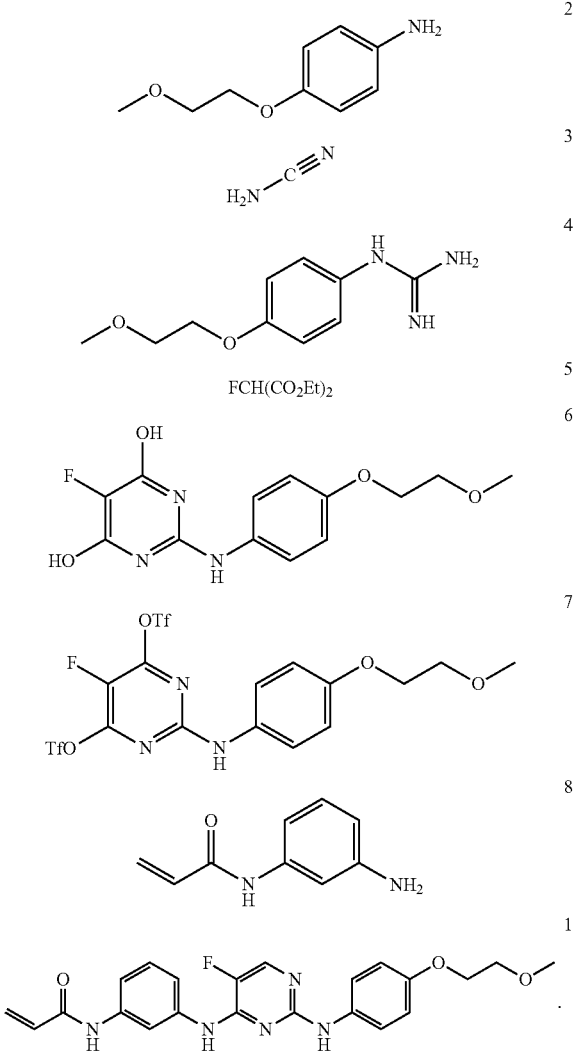

20 Claims, No Drawings

SYNTHESIS OF N-(3-(5-FLUORO-2-(4-(2-METHOXYETHOXY)PHENYLAMINO)PYRIMIDIN-4-YLAMINO)PHENYL) ACRYLAMIDE

FIELD

The present invention refers to a chemical medicine field, it relates generally to the synthesis of BTK inhibitor, specifically, the invention relates to method for preparing BTK inhibitor CC-292.

BACKGROUND

Bruton's tyrosine kinase (abbreviated Btk or BTK) also known as tyrosine-protein kinase BTK is an enzyme that in humans is encoded by the BTK gene. BTK was discovered in 1993 and is named for Ogden Bruton, who first described XLA in 1952. BTK is a kinase that plays a crucial role in B-cell development. Its exact mechanism of action remains unknown, but it plays a crucial role in B cell maturation as well as mast cell activation through the high-affinity IgE receptor. Btk contains a PH domain that binds phosphatidylinositol (3,4,5)-trisphosphate (PIP3). PIP3 binding induces Btk to phosphorylate phospholipase C, which in turn hydrolyzes PIP2, a phosphatidylinositol, into two second messengers, inositol triphosphate (IP3) and diacylglycerol (DAG), which then go on to modulate the activity of downstream proteins during B-cell signalling.

Ibrutinib (PCI-32765), the first selective BTK inhibitor, was approved by the US FDA in November 2013 for the treatment of mantle cell lymphoma and in February 2014 for the treatment of chronic lymphocytic leukemia.

Celgene (following its acquisition of Avila) is developing spebrutinib (CC-292, AVL-292, structure shown), the lead from a series of Bruton's tyrosine kinase (Btk) inhibitors, including CNX-652, for the potential oral treatment of B-cell cancers such as non-Hodgkin's lymphoma (NHL) and chronic lymphocytic leukemia (CLL), diffuse large B-cell lymphoma (DLBCL), B-cell mediated autoimmune diseases such as rheumatoid arthritis (RA) and multiple myeloma. In October 2013, a phase II RA trial began. In June 2011, a phase Ib trial in B-cell cancers was initiated; in February 2013, a phase I trial in CLL/small lymphocytic leukemia (SLL) began. In December 2013, a phase I trial was initiated in DCBCL patients in the US, France and Italy. In January 2014, initial data from a phase I/II study of spebrutinib in combination with lenalidomide in CLL patients were expected in 2014.

CC-292 is described chemically as N-(3-(5-fluoro-2-(4-(2-methoxyethoxyl)phenylamino)pyrimidin-4-ylamino)phenyl)acrylamide, and has the structural formula shown as Formula 1:

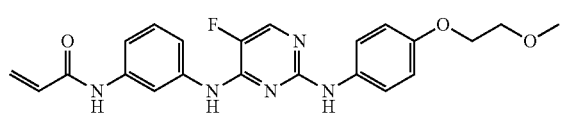

1

Patent application publication No. US2010029610A1 disclose preparation method of CC-292 and closely related analogues. The synthetic route of CC-292 is shown below.

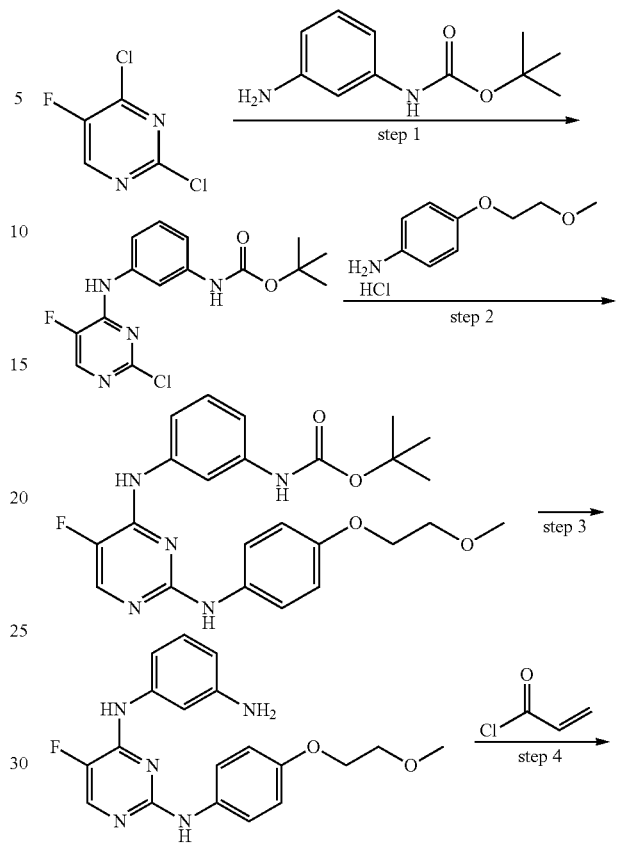

Formula 1 (CC-292)

In the first step of US2010029610A1, it's easy to produce 2-substituted and 2,4-bis substituted products with low yield and difficult to separate.

DESCRIPTION OF THE DISCLOSURE

It is an object of the present disclosure to devise a method for preparing BTK inhibitor to improve the process for the synthesis of BTK inhibitor CC-292, thereby avoiding at least one of the disadvantages described above.

It has now been found, surprisingly, in the present disclosure, through control the amount of the intermediate N-(3-aminophenyl)acrylamide, inventors can effectively control the 2,4-bis-substituted product in the preparation of CC-292. Because of high polarity, small amount 2,4-bis-substituted product can easily remove by recrystallization. The whole reaction route is simple and easy to control, does not use harsh conditions such as high temperature and high pressure, and high yield.

The term "contacting" herein should be understood broadly, allowing any of at least two reactants react; for example, two reactants to be mixed under appropriate condition. According to the experimental requirements, mixing the reactants with which need to be contacted under stirring. Therefore, the type of agitation is not particularly limited. For example, may be a mechanical agitation, i.e. under the action of mechanical forces stirring.

As used herein, "a compound of formula N" is sometimes also referred to "Compound N". For example, "a compound of formula 2" may also be referred to "compound 2".

In this article, the term "first" or "second" is only used for describing objective other than indicate or imply relative importance or implicit indicate the number of technical features or technical solutions. Thus, defining the "first", the "second" features may explicitly or implicitly includes one or more of the characteristics. In the description of the disclosure, "multiple" means two or more, unless otherwise specifically limited.

According to the present disclosure, it is devised a process of preparing a compound of formula 1 (CC-292):

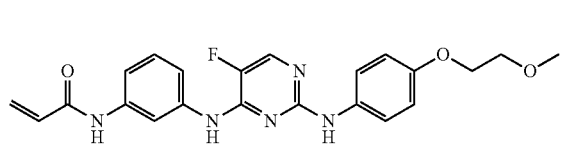

1

The technical solutions of the present disclosure include: a compound 4 is prepared by a process comprising reacting a compound 2 with a compound 3, a compound 6 is prepared by a process comprising reacting the compound 4 with a compound 5, a compound 7 is prepared by a process comprising reacting the compound 6 with trifluoromethanesulfonic anhydride ($Tf_2O$), the compound 1 (CC-292) is prepared by a process comprising reacting the compound 7 with a compound 8.

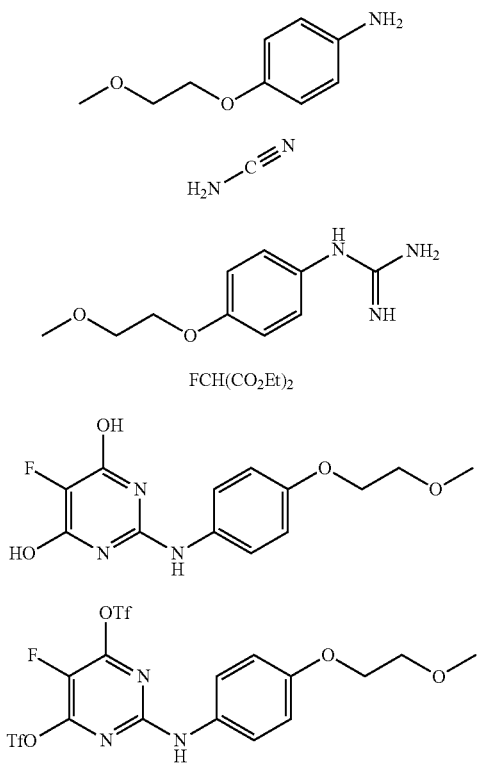

According to an embodiment of the present disclosure, the preparation method of CC-292 includes the following steps:

Step (1): contacting a compound of formula 2 with a compound of formula 3 to obtain a compound of formula 4.

Step (2): contacting the compound of formula 4 with a compound of formula 5 to obtain a compound of formula 6.

Step (3): contacting the compound of formula 6 with trifluoromethanesulfonic anhydride to obtain a compound of formula 7.

Step (4): contacting the compound of formula 7 with a compound of formula 8 to obtain the compound of formula 1.

In some embodiments, in the method disclosed herein, the preparation method of the present disclosure is as follows.

According to some embodiments of the present disclosure, in the step (A), the compound 4 may be prepared according to the method described in Bioorganic & Medicinal Chemistry Letters, 2004, 14(16), 4237-4240, which is incorporated by reference, the yield of the compound 4 is over 90%.

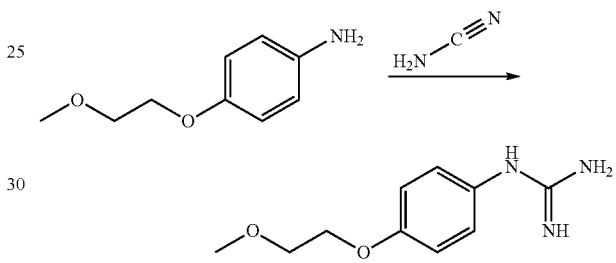

According to some embodiments of the present disclosure, the compound of formula 4 is contacted with the compound of formula 5 under a non-oxidizing atmosphere. In some embodiments, the non-oxidizing atmosphere is nitrogen atmosphere, helium atmosphere, or a combination thereof.

According to some embodiments of the present disclosure, the compound of formula 4 is contacted with the compound of formula 5 in a first organic solvent. In some embodiments, the first organic solvent is N,N-dimethyl formamide.

According to some embodiments of the present disclosure, the compound of formula 4 is contacted with the compound of formula 5 under a temperature ranging about 60° C. to about 80° C. for about 6 hours to about 8 hours.

According to some embodiments of the present disclosure, in the step (2), the compound 4, the compound 5 and DMF are added into a first reactor, then the first reactor is sealed under nitrogen atmosphere, and the resulting mixture is kept at 60° C.~80° C., stirred for 6 to 8 hours. After cooling to room temperature, the resulting mixture is diluted with acetic ether and filtered. The filtrate is washed twice with water, and the combined aqueous phases are extracted twice with acetic ether. The organic layers are combined, dried over $Na_2SO_4$, and concentrated to obtain the compound 6.

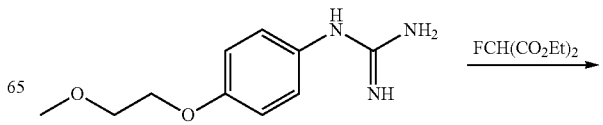

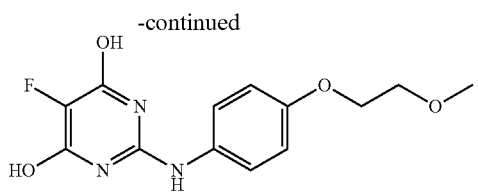

According to some embodiments of the present disclosure, in the method disclosed herein, the compound 5 in step (2) may be used at an amount of 1.0 equivalent to 1.5 equivalents per 1 equivalent by mole of compound 4. In some other embodiments, the amount is 1.05 equivalents per 1 equivalent by mole of the compound 4.

According to some embodiments of the present disclosure, the compound of formula 6 is contacted with trifluoromethanesulfonic anhydride in a second organic solvent. In some embodiments, the second organic solvent is dichloromethane.

According to some embodiments of the present disclosure, the compound of formula 6 is contacted with trifluoromethanesulfonic anhydride under room temperature for about 3 hours to about 6 hours.

According to some embodiments of the present disclosure, in the step (3), the compound 6, Tf₂O and dichloromethane are added into a second reactor, and the resulting mixture is kept at room temperature (25° C.), stirred for 3 to 6 hours. The resulting mixture is diluted with dichloromethane and filtered. The filtrate is washed twice with water, and the combined aqueous phases are extracted twice with dichloromethane. The organic layers are combined, dried over Na₂SO₄, and concentrated to obtain the compound 7.

equivalent by mole of the compound 6. In some other embodiments, the amount is 2.1 equivalents per 1 equivalent by mole of the compound 6.

According to some embodiments of the present disclosure, the compound of formula 7 is contacted with the compound of formula 8 in a third organic solvent, and in presence of N,N-diisopropylethylamine and a base. In some embodiments, the third organic solvent is dichloromethane. In some other embodiments, the base is NaHCO₃, KHCO₃, Na₂CO₃, Cs₂CO₃, K₂CO₃, K₃PO₄, or a combination thereof.

According to some embodiments of the present disclosure, step (4) comprises: contacting the compound of formula 7 with the compound of formula 8 in presence of the third organic solvent, N,N-diisopropylethylamine, and the base; and adjusting a pH of the resulting reaction mixture to about 1.0 to about 2.0 with hydrochloric acid solution.

According to some embodiments of the present disclosure, in the step (4), the compound 7, the compound 8, N,N-diisopropylethylamine (DIEA), dichloromethane and a first base are added into a third reactor, and the resulting mixture is kept at room temperature (25° C.), stirred for 0.5 to 2 hours. Then, hydrochloric acid solution is slowly added to the resulting mixture to adjust the pH to 1~2, then the resulting mixture is filtered. The filtrate is washed twice with water, and the combined aqueous phases are extracted twice with dichloromethane. The organic layers are combined, dried over Na₂SO₄, and concentrated to get crude product of CC-292. Then the crude product is stirred with methanol/acetone (V:V=2:1) and crystallized at 0° C.~5° C. for 3~5 hours. The filter cake is dried in vacuo at 60° C. for 8 hours to obtain the CC-292 product (compound 1) as a white solid.

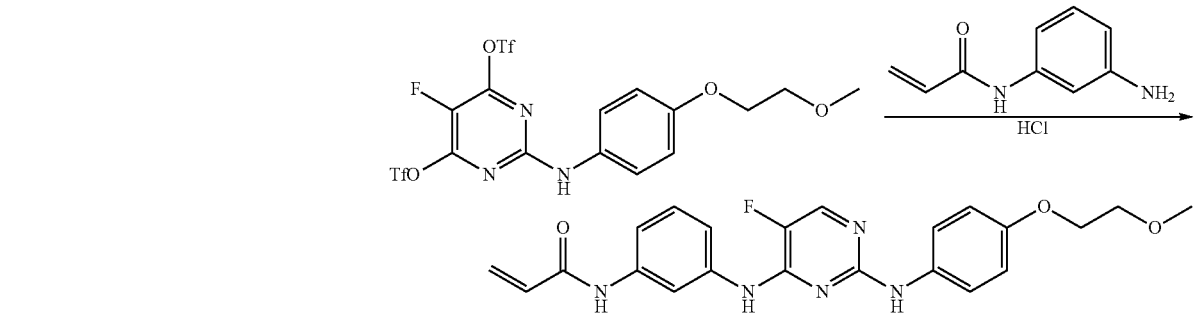

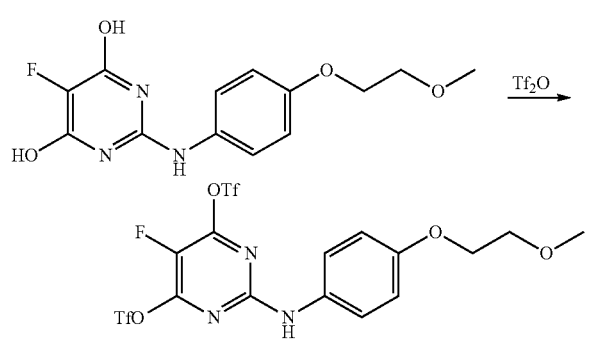

According to some embodiments of the present disclosure, in the method disclosed herein, Tf₂O in step (3) may be used at an amount of 2.0 equivalents to 4.0 equivalents per 1

According to some embodiments of the present disclosure, in the method disclosed herein, the compound 8 in step (4) may be used at an amount of 1.0 equivalent to 1.2 equivalents per 1 equivalent by mole of the compound 7. In some other embodiments, the amount is 1.1 equivalents per 1 equivalent by mole of the compound 7.

According to some embodiments of the present disclosure, in the method disclosed herein, DIEA in step (4) may be used at an amount of 1.0 equivalent to 1.5 equivalents per 1 equivalent by mole of the compound 7. In some other embodiments, the amount is 1.2 equivalents per 1 equivalent by mole of the compound 7. According to some embodiments of the present disclosure, the method foe preparing the compound of formula 1 comprises: (a) contacting the compound of formula 2 with the compound of formula 3 to obtain the compound of formula 4; (b) dissolving the compound of formula 4, 20.9 g, 0.1 mol, the compound of formula 5, 18.7 g, 0.105 mol in N,N-dimethyl formamide 200 mL; (c) keeping the resulting mixture of step (b) at 70° C. with stirring for 7 hours under nitrogen atmosphere, to obtain the compound of formula 6; (d) dissolving the compound of formula 6, 29.5 g, 0.1 mol, trifluoromethanesulfonic anhydride, 59.2 g, 0.21 mol in dichloromethane 240 mL; (e) keeping the resulting mixture of step (d) at 25° C. with stirring for 4 hours, to obtain the compound of formula 7; (f) dissolving the compound of formula 7, 29.5 g, 0.1 mol, the compound of formula 8, 19.44 g, 0.12 mol, N,N-diisopropylethylamine 13.0 g, 0.1 mol and $KHCO_3$ 20.0 g, 0.2 mol in dichloromethane 500 mL; (g) keeping the resulting mixture of step (f) at 25° C. with stirring for 0.5 hour; and (h) adjusting a pH of the resulting mixture of step (g) to about 1.0 to about 2.0 with hydrochloric acid solution, to obtain the compound of formula 1.

In the present invention, the term "comprise" is an open expression, it means comprising the contents disclosed herein, but don't exclude other contents.

Compared with the prior art, the advantages of the present invention is as follows:

(i) In the first step of patent US2010029610A1, it's easy to produce 2-substituted and 2,4-bis substituted products and with low yield, and it's difficult to separate. But in the present invention, competitive reaction between 2-bit and 4-bit is not exist. Through controlling the amount of aniline, inventors can effectively control the 2,4-bis-substituted product. Because of high polarity, small amount 2,4-bis-substituted product can be easily removed by recrystallization.

(ii) The whole reaction route is simple, easy to control and has high yield, and does not use harsh conditions such as high temperature and high pressure.

(iii) Do not need the protecting group in the patent and the process of removing the protecting group and reduce the generation of solid and liquid wastes.

EXAMPLES

The new preparation methods of BTK inhibitor CC-292 and intermediates thereof are disclosed in the examples of the present disclosure. Those skilled in the art can learn from this article to properly improve the process parameters to implement the preparation method. It's to note that all the similar replacements and changes are obvious for the skilled person and within the scope of the present disclosure. The methods disclosed herein are described in the preferred examples. Related persons can clearly realize and apply the techniques disclosed herein by making some changes, appropriate alterations or combinations to the methods without departing from spirit, principles and scope of the present disclosure.

In order to further understand the invention, it is detailed below through examples.

Example 1

Preparation of Compound 6

Compound 4 (20.9 g, 0.1 mol), compound 5 (17.8 g, 0.1 mol) and DMF (200 mL) were added into a reactor, then the reactor was sealed under nitrogen atmosphere, and the resulting mixture was kept at 80° C., stirred for 6 hours. After cooling to room temperature, the mixture was diluted with acetic ether (100 mL) and filtered. The filtrate was washed twice with water (2×100 mL), and the combined aqueous phases were extracted twice with acetic ether (2×100 mL). The organic layers were combined, dried over $Na_2SO_4$, and concentrated to obtain compound 6 (26.0 g, yield 88.1%).

Example 2

Preparation of Compound 6

Compound 4 (20.9 g, 0.1 mol), compound 5 (18.7 g, 0.105 mol) and DMF (200 mL) were added into a reactor, then the reactor was sealed under nitrogen atmosphere, and the resulting mixture was kept at 70° C., stirred for 7 hours. After cooling to room temperature, the mixture was diluted with acetic ether (100 mL) and filtered. The filtrate was washed twice with water (2×100 mL), and the combined aqueous phases were extracted twice with acetic ether (2×100 mL). The organic layers were combined, dried over $Na_2SO_4$, and concentrated to obtain compound 6 (26.7 g, yield 90.5%).

Example 3

Preparation of Compound 6

Compound 4 (20.9 g, 0.1 mol), compound 5 (26.7 g, 0.15 mol) and DMF (200 mL) were added into a reactor, then the reactor was sealed under nitrogen atmosphere, and the resulting mixture was kept at 60° C., stirred for 8 hours. After cooling to room temperature, the mixture was diluted with acetic ether (100 mL) and filtered. The filtrate was washed twice with water (2×100 mL), and the combined aqueous phases were extracted twice with acetic ether (2×100 mL). The organic layers were combined, dried over $Na_2SO_4$, and concentrated to obtain compound 6 (26.4 g, yield 89.4%).

Example 4

Preparation of Compound 7

Compound 6 (29.5 g, 0.1 mol), $Tf_2O$ (56.4 g, 0.2 mol) and dichloromethane (240 mL) were added into a reactor, and the resulting mixture was kept at 25° C., stirred for 6 hours. Then the mixture was diluted with dichloromethane (100 mL) and filtered. The filtrate was washed twice with water (2×100 mL), and the combined aqueous phases were extracted twice with dichloromethane (2×100 mL). The organic layers were combined, dried over $Na_2SO_4$, and concentrated to obtain compound 7 (51.5 g, yield 92.1%).

Example 5

Preparation of Compound 7

Compound 6 (29.5 g, 0.1 mol), $Tf_2O$ (59.2 g, 0.21 mol) and dichloromethane (240 mL) were added into a reactor, and the resulting mixture was kept at 25° C., stirred for 4 hours. Then the subsequent processing was as the same as example 4, to obtain compound 7 (52.7 g, yield 94.2%).

Example 6

Preparation of Compound 7

Compound 6 (29.5 g, 0.1 mol), $Tf_2O$ (56.4 g, 0.4 mol) and dichloromethane (240 mL) were added into a reactor, and the mixture was kept at 25° C., stirred for 3 hours. Then the subsequent processing was as the same as example 4, to obtain compound 7 (50.6 g, yield 90.5%).

Example 7

Preparation of CC-292

Compound 7 (29.5 g, 0.1 mol), compound 8 (16.2 g, 0.1 mol), DIEA (15.5 g, 0.12 mol), dichloromethane (500 mL)

and NaHCO$_3$ (16.8 g, 0.2 mol) were added into a reactor, and the resulting mixture was kept at 25° C., stirred for 2 hours. Then hydrochloric acid solution was slowly added to the mixture to adjust the pH to 1~2, then the mixture was filtered. The filtrate was washed twice with water, and the combined aqueous phases were extracted twice with dichloromethane. The organic layers were combined, dried over Na$_2$SO$_4$, and concentrated to get crude product of CC-292. Then the crude product was stirred with methanol/acetone (V:V=2:1) and crystallized at 0° C. for 3 hours. The filter cake was dried in vacuo at 60° C. for 8 hours to obtain the CC-292 product (compound 1) as a white solid (26.0 g, yield 61.4%), HPLC purity: 99.2%. $^1$H NMR (DMSO-d6) δ ppm: 2.27 (s, 3H), 5.72 (d, J=9.84 Hz, 1H), 6.22 (d, J=16.92 Hz, 1H), 6.44 (dd, J=10.2, 17.02 Hz, 1H), 6.85 (d, J=7.12 Hz, 1H), 7.12-7.19 (m, 2H), 7.29 (d, J=7.68 Hz, 1H), 7.43 (d, J=7.92 Hz, 1H), 7.61-7.63 (m, 2H), 7.82 (s, 1H), 8.08 (s, 1H), 9.23 (bs, 2H), 10.03 (s, 1H); LCMS: m/e 364.2 (M+1).

Example 8

Preparation of CC-292

Compound 7 (29.5 g, 0.1 mol), compound 8 (19.44 g, 0.12 mol), DIEA (13.0 g, 0.1 mol), dichloromethane (500 mL) and KHCO$_3$ (20.0 g, 0.2 mol) were added into a reactor, and the resulting mixture was kept at 25° C., stirred for 0.5 hour. Then hydrochloric acid solution was slowly added to the mixture to adjust the pH to 1~2, then the mixture was filtered. The filtrate was washed twice with water, and the combined aqueous phases were extracted twice with dichloromethane. The organic layers were combined, dried over Na$_2$SO$_4$, and concentrated to get crude product of CC-292. Then the crude product was stirred with methanol/acetone (V:V=2:1) and crystallized at 2° C. for 4 hours. The filter cake was dried in vacuo at 60° C. for 8 hours to obtain the CC-292 product (compound 1) as a white solid (27.1 g, yield 64.0%), HPLC purity: 99.7%.

Example 9

Preparation of CC-292

Compound 7 (29.5 g, 0.1 mol), compound 8 (17.8 g, 0.11 mol), DIEA (19.4 g, 0.15 mol), dichloromethane (500 mL) and Na$_2$CO$_3$ (21.2 g, 0.2 mol) were added into a reactor, and the resulting mixture was kept at 25° C., stirred for 1 hours. Then hydrochloric acid solution was slowly added to the mixture to adjust the pH to 1~2, then the mixture was filtered. The filtrate was washed twice with water, and the combined aqueous phases were extracted twice with dichloromethane. The organic layers were combined, dried over Na$_2$SO$_4$, and concentrated to get crude product of CC-292. Then the crude product was stirred with methanol/acetone (V:V=2:1) and crystallized at 5° C. for 3 hours. The filter cake was dried in vacuo at 60° C. for 8 hours to obtain the CC-292 product (compound 1) as a white solid (24.5 g, yield 57.8%), HPLC purity: 99.5%.

In the specification, unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing a compound of formula 1, comprising:
   (1) contacting a compound of formula 2 with a compound of formula 3 to obtain a compound of formula 4;
   (2) contacting the compound of formula 4 with a compound of formula 5 to obtain a compound of formula 6;
   (3) contacting the compound of formula 6 with trifluoromethanesulfonic anhydride to obtain a compound of formula 7; and
   (4) contacting the compound of formula 7 with a compound of formula 8 to obtain the compound of formula 1,

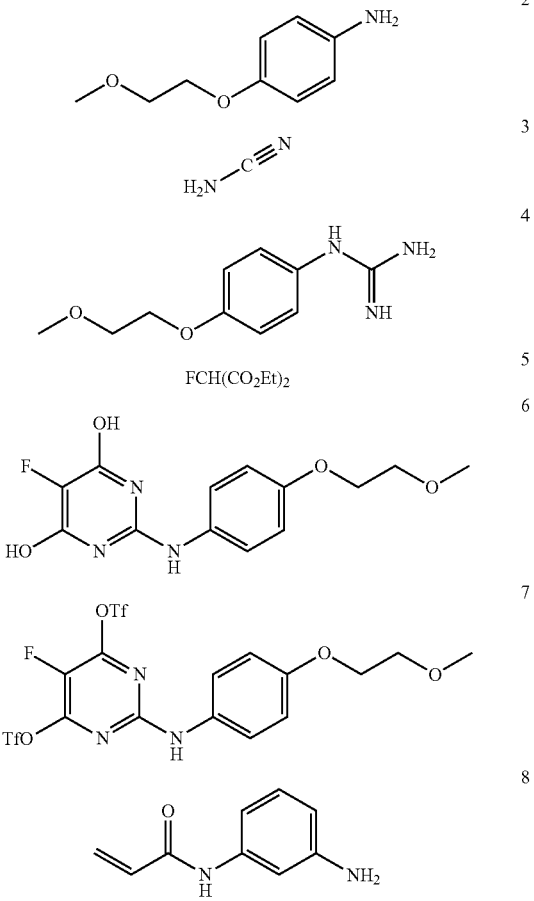

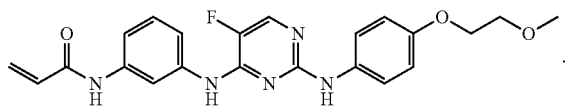

2. The method of claim 1, wherein the compound of formula 4 is contacted with the compound of formula 5 under a non-oxidizing atmosphere.

3. The method of claim 2, wherein the non-oxidizing atmosphere is nitrogen atmosphere, helium atmosphere, or a combination thereof.

4. The method of claim 1, wherein the compound of formula 4 is contacted with the compound of formula 5 in a first organic solvent, and the first organic solvent is N,N-dimethyl formamide.

5. The method of claim 4, wherein the compound of formula 4 is contacted with the compound of formula 5 under a temperature ranging about 60° C. to about 80° C. for about 6 hours to about 8 hours.

6. The method of claim 5, wherein the amount of the compound of formula 5 is 1.00 equivalent to 1.50 equivalents per 1 equivalent by mole of the compound of formula 4.

7. The method of claim 6, wherein the amount of the compound of formula 5 is 1.05 equivalents per 1 equivalent by mole of the compound of formula 4.

8. The method of claim 1, wherein the compound of formula 6 is contacted with trifluoromethanesulfonic anhydride in a second organic solvent, and the second organic solvent is dichloromethane.

9. The method of claim 8, wherein the compound of formula 6 is contacted with trifluoromethanesulfonic anhydride under room temperature for about 3 hours to about 6 hours.

10. The method of claim 9, wherein the amount of trifluoromethanesulfonic anhydride is 2.0 equivalents to 4.0 equivalents per 1 equivalent by mole of the compound of formula 6.

11. The method of claim 10, wherein the amount of trifluoromethanesulfonic anhydride is 2.1 equivalents per 1 equivalent by mole of the compound of formula 6.

12. The method of claim 1, wherein the compound of formula 7 is contacted with the compound of formula 8 in a third organic solvent, and in presence of N,N-diisopropylethylamine and a base.

13. The method of claim 1, wherein step (4) comprises:
contacting the compound of formula 7 with the compound of formula 8 in presence of a third organic solvent, N,N-diisopropylethylamine, and a base; and
adjusting a pH of the resulting reaction mixture to about 1.0 to about 2.0 with hydrochloric acid solution.

14. The method of claim 13, wherein the third organic solvent is dichloromethane, and the base is $NaHCO_3$, $KHCO_3$, $Na_2CO_3$, $Cs_2CO_3$, $K_2CO_3$, $K_3PO_4$, or a combination thereof.

15. The method of claim 13, wherein the compound of formula 7 is contacted with the compound of formula 8 under room temperature with stirring for about 0.5 hour to about 2 hours.

16. The method of claim 13, wherein the amount of the compound of formula 8 is 1.0 equivalent to 1.2 equivalents per 1 equivalent by mole of the compound of formula 7.

17. The method of claim 16, wherein the amount of the compound of formula 8 is 1.1 equivalents per 1 equivalent by mole of the compound of formula 7.

18. The method of claim 13, wherein the amount of N,N-diisopropylethylamine is 1.0 equivalent to 1.5 equivalents per 1 equivalent by mole of the compound of formula 7.

19. The method of claim 18, wherein the amount of N,N-diisopropylethylamine is 1.2 equivalents per 1 equivalent by mole of the compound of formula 7.

20. The method of claim 1, wherein:
step (2) is performed by
(a) dissolving 20.9 g (0.1 mol) of the compound of formula 4 and 18.7 g (0.105 mol) of the compound of formula 5 in 200 mL of N,N-dimethylformamide, and
(b) keeping the resulting mixture of step (a) at 70° C. with stirring for 7 hours under nitrogen atmosphere, to obtain the compound of formula 6;
step (3) is performed by
(c) dissolving 29.5 g (0.1 mol) of the compound of formula 6 and 59.2 g (0.21 mol) of trifluoromethanesulfonic anhydride in 240 mL of dichloromethane, and
(d) keeping the resulting mixture of step (c) at 25° C. with stirring for 4 hours, to obtain the compound of formula 7; and
step (4) is performed by
(e) dissolving 29.5 g (0.1 mol) of the compound of formula 7, 19.44 g (0.12 mol) of the compound of formula 8, 13.0 g (0.1 mol) of N,N-diisopropylethylamine and 20.0 g (0.2 mol) of $KHCO_3$ in 500 mL of dichloromethane,
(f) keeping the resulting mixture of step (e) at 25° C. with stirring for 0.5 hour, and
(g) adjusting a pH of the resulting mixture of step (f) to about 1.0 to about 2.0 with hydrochloric acid solution, to obtain the compound of formula 1.

* * * * *